United States Patent [19]

Bryant et al.

[11] Patent Number: 5,622,972

[45] Date of Patent: Apr. 22, 1997

[54] METHOD FOR TREATING A MAMMAL INFECTED WITH RESPIRATORY SYNCYTIAL VIRUS

[75] Inventors: Martin L. Bryant, Chesterfield, Mo.; Francis J. Koszyk, Prospect Heights, Ill.; Richard A. Mueller, Glencoe, Ill.; Richard A. Partis, Evanston, Ill.

[73] Assignee: G. D. Searle & Co., Chicago, Ill.

[21] Appl. No.: 585,603

[22] Filed: Jan. 26, 1996

Related U.S. Application Data

[63] Continuation of Ser. No. 201,537, Feb. 25, 1994, abandoned.

[51] Int. Cl.$^6$ .................................................. A61K 31/445
[52] U.S. Cl. ............................................ 514/315; 514/328
[58] Field of Search ..................................... 514/315, 328

[56] References Cited

U.S. PATENT DOCUMENTS

| | | | |
|---|---|---|---|
| 4,246,345 | 1/1981 | Kinast et al. | 435/84 |
| 4,266,025 | 5/1981 | Kinast et al. | 435/84 |
| 4,405,714 | 9/1983 | Kinast et al. | 435/84 |
| 4,806,650 | 2/1989 | Schroeder et al. | 435/84 |
| 4,957,926 | 9/1990 | Jacob et al. | 514/315 |
| 5,003,072 | 3/1991 | Partis et al. | 514/315 |
| 5,030,638 | 7/1991 | Partis et al. | 514/315 |
| 5,144,037 | 9/1992 | Partis et al. | 514/315 |
| 5,221,746 | 6/1993 | Partis et al. | 514/315 |

OTHER PUBLICATIONS

Ayisi, N., et al., Modified tetrazolium–based colorimetric method for determining the activities of anti–HIV compounds, *J. Virological Methods*, 33, 335–344 (1991).

Bryant, M., et al., Efficacy and Safety of α–Glucosidase Inhibitor Prodrug SC–49483 in Rhesus Monkeys Infected with SIV, 10th Intl. Conference of AIDS, Jun. 7–11, 1993, Abstract No. WS–A11–2.

Filippell, M., et al., Respiratory Syncytial Virus, *Infection Control*, 28, 651–671 (1993).

Hodes, D.S., et al., Inhibition of Respiratory Syncytial, Parainfluenza 3 and Measles Viruses by 2–Deoxy–D–Glucose, *Virology*, 63, 201–208 (1975).

LaVia, W., et al., Respiratory syncytial virus puzzle: Clinical features, pathophysiology, treatment, and prevention, *J. Pediatrics*, 121, 503, 510 (1992).

McIntosh, K., and Chanock, R., Respiratory Syncytial Virus, Chap. 38 in *Virology*, Second Edition, B. Fields, et al., (eds), Raven Press Ltd., New York, N.Y. (1990).

Rubino, K., et al., A novel, spectophotometric microneutralization assay for respiratory syncytial virus, *J. Virological Methods*, 39, 55–67 (1992).

Schnitzer, T., et al., Effect of 2–Deoxy–D–Glucose and Glucosamine on the Growth and Functions of Respiratory Syncytial and Parainfluenza 3 Viruses, *Virology*, 67, 306–309 (1975).

Stretton, M., et al., Intensive Care Course and Outcome of Patients Infected With Respiratory Syncytial Virus, *Pediatric Pulmonol.*, 13, 143–150 (1992).

Primary Examiner—Jerome D. Goldberg
Attorney, Agent, or Firm—Fitzpatrick, Cella, Harper & Scinto

[57] ABSTRACT

A method is provided for treating a mammal infected with respiratory syncytial virus (RSV) comprising administering to the mammal an RSV inhibitory effective amount of a compound or its pharmaceutically acceptable salt of the formula

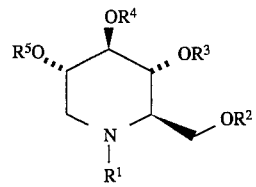

wherein $R^1$ is alkyl, aralkyl, aroyl or acyl and $R^2$, $R^3$, $R^4$ and $R^5$ are H or acyl.

12 Claims, No Drawings

METHOD FOR TREATING A MAMMAL INFECTED WITH RESPIRATORY SYNCYTIAL VIRUS

This is a CONTINUATION of application Ser. No. 08/201,537, filed Feb. 25, 1994, abandoned.

BACKGROUND OF THE INVENTION

Respiratory syncytial virus (RSV) infects the general population each winter. While RSV infection affects and inconveniences otherwise healthy adults with symptoms of the common cold, it produces especially serious symptoms in infants and young children. Essentially all children are infected with respiratory syncytial virus before the age of 3, and RSV can cause severe bronchiolitis or pneumonia, progressing to morbid disease or death in a significant percentage of children. See K. McIntosh and R. Chanock, *Respiratory Syncytial Virus*, Chap. 38, in B. Fields et al. (eds.), Virology, Second Edition, Raven Press, Ltd., New York, N.Y. (1990); W. LaVia et al., J. Pediatrics, 121, 503–510 (1992); M. Stretton et al., Pediatr. Pulmonol. 13, 143–150 (1992); and M. Filippell et al., Infection Control 28, 651–671 (1993).

The only drug to be approved by the U.S. Food and Drug Administration (FDA) for treatment of respiratory syncytial virus (RSV) is ribavirin, 1-beta-D-ribofuranosyl-1H-1,2,4-triazole-3-carboxamide. This nucleoside analog was originally selected as a potential antiviral compound effective against RSV by in vitro testing. Such in vitro tests are useful and virtually the only practical method of initially screening and testing potential anti-RSV drugs. A serious drawback of ribavirin is that it must be inhaled as an aerosol which, for infants and young children, means that it must be administered in an enclosed atmosphere. Moreover, ribavirin has toxic side-effects. Thus, there is a need for improved anti-RSV drugs, especially drugs which do not need to be administered by aerosol and preferably can be delivered orally.

SUMMARY OF THE INVENTION

In accordance with the present invention a method for treating a mammal infected with respiratory syncytial virus comprising administering to the mammal having a disease caused by respiratory syncytial virus (RSV) an RSV inhibitory effective amount of a compound, for an amount of time sufficient to inhibit or eliminate the disease caused by RSV, the compound being selected from the group consisting of 1,5-dideoxy-1,5-imino-D-glucitol or an N-alkyl, N-acyl, N-aroyl, N-aralkyl and/or O-acylated derivative thereof. The above-defined compounds have been found to have useful antiviral activity against respiratory syncytial virus.

DETAILED DESCRIPTION OF THE INVENTION

In one of its aspects the present invention entails administration of an RSV inhibitory effective amount of 1,5-dideoxy-1,5-imino-D-glucitol or an N-substituted and/or O-acylated derivative thereof to a mammal infected with respiratory syncytial virus. An "RSV inhibitory effective amount" of a compound disclosed herein is an amount of a disclosed compound which inhibits respiratory syncytial virus and does not exhibit adverse toxic effects outweighing the benefit of virus inhibition.

1,5-dideoxy-1,5-imino-D-glucitol is a six-membered heterocyclic compound having nitrogen in the ring and four hydroxyl groups. It is thus described by a systematic chemical name as a sugar derivative in which the six-membered ring is considered as a mimic of pyranose, with nitrogen instead of oxygen in the ring. It can also be described structurally as a derivative of piperidine.

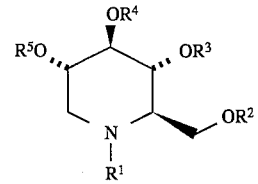

1,5-dideoxy-1,5-imino-D-glucitol ($R^1 = R^2 = R^3 = R^4 = R^5 = H$)

The free hydroxyl groups on 1,5-dideoxy-1,5-imino-D-glucitol and the N-substituted derivatives thereof may preferably be acylated with up to four, preferably exactly four, O-acyl groups. It is presently preferred to provide the compounds for use in accordance with the present invention as the peracylated derivatives. O-acylated 1,5-dideoxy-1,5-imino-D-glucitol and its N-substituted derivatives may be referred to as "prodrugs". The O-acyl groups are enzymatically removed to provide the non-O-acylated (i.e., hydroxy-containing N-substituted or unsubstituted 1,5-dideoxy-1,5-imino-D-glucitol compounds) in vivo. M. Bryant et al., 10th International Conference of AIDS, Berlin, Jun. 7–11, 1993, Abstr. No. WS-A11-2.

With respect to the O-acyl groups, $R^2$, $R^3$, $R^4$ and $R^5$ may individually be an acyl moiety represented by the formula

wherein $R^6$ is a linear or branched $C_1$–$C_{10}$ alkyl moiety including but not limited to methyl, ethyl, propyl, isopropyl, butyl, pentyl, hexyl, nonyl, a $C_3$–$C_7$ cycloalkyl, or a $C_4$–$C_{10}$ cycloalkylalkyl including but not limited to (cyclopropyl)methyl, (cyclopropyl)ethyl, (cyclobutyl)ethyl, (cyclopentyl)ethyl, (cyclohexyl)methyl, (cyclohexyl)ethyl and the like.

The N-alkyl groups may be linear or branched $C_1$–$C_{14}$ alkyl group, more preferably $C_1$–$C_9$ and most preferably a $C_4$–$C_9$ alkyl group including but not limited to methyl, ethyl, propyl, isopropyl, butyl, pentyl, hexyl, nonyl, 2-ethylbutyl and 2-methylpentyl and the like.

The N-acyl groups include but are not limited to methyl malonyl, ethyl malonyl and the like.

The N-aralkyl groups may have from about 7 to about 14 carbon atoms and include but are not limited to phenylalkyl moieties wherein the alkyl moiety is a linear or branched $C_1$–$C_8$ alkyl, such as benzyl, phenethyl, 3-phenylpropyl, 2-phenylpropyl, butylphenyl, hexylphenyl, 3-phenyloctyl and the like.

The N-aroyl groups may have from about 7–14 carbons and include but are not limited to phenylacetyl, benzyloxycarbonyl, benzoyl, biphenylacetyl, phenoxyacetyl, chlorophenylacetyl, hydrocinnamoyl, cinnamoyl, and the like, and pyridinylcarbonyl moieties such as nicotinoyl.

The aryl or aroyl groups can have one or more, preferably 1 to 3, identical or different substituents. Examples of substituents are alkyl or alkoxy having from one to six carbon atoms; halogen such as Cl, Br or F; and hydroxyl.

The following reaction schemes describe presently preferred methods for making the N-alkyl, N-aralkyl, N-aroyl, N-acyl and/or O-acylated derivatives of 1,5-dideoxy-1,5-imino-D-glucitol. The compound 1,5-dideoxy-1,5-imino-D-glucitol is alternatively referred to herein as "1-deoxynojirimycin" or simply "DNJ." DNJ is well known and commercially available from a variety of chemical manufacturers, e.g., ICN Biochemicals Inc., Costa Mesa, Calif. (Cat. #150819); Chemical Dynamics Corporation, South Plainfield, N.J. (Cat. #26-9415-00). In addition, various methods for synthesis of 1-deoxynojirimycin and N-substituted derivatives thereof are disclosed in U.S. Pat. Nos. 4,246,345; 4,266,025; 4,405,714; 4,806,650; and in U.S. patent application Ser. No. 07/851,818, filed Mar. 16, 1992. The contents of each of the above documents is hereby incorporated by reference into this document.

SCHEME 1

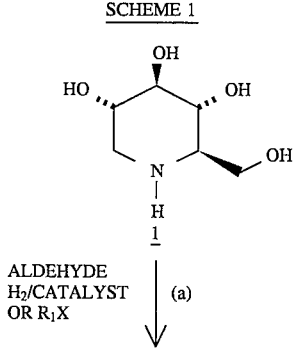

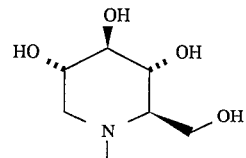

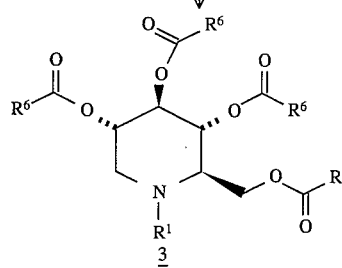

-continued
SCHEME 1

SCHEME 2

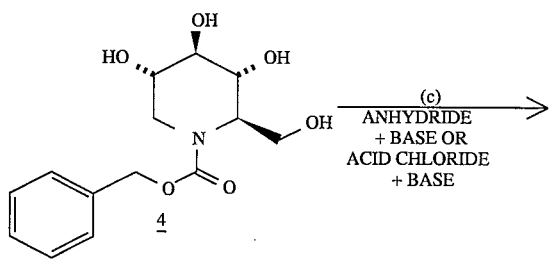

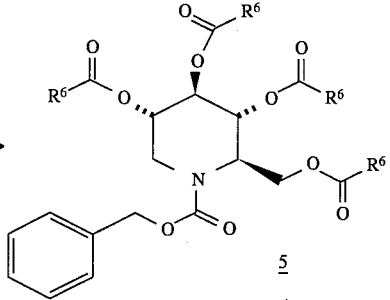

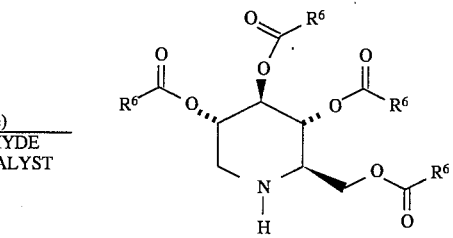

SCHEME 2 (continued)

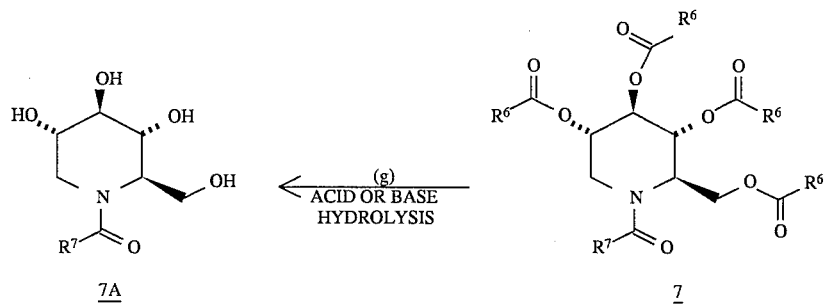

SCHEME 3

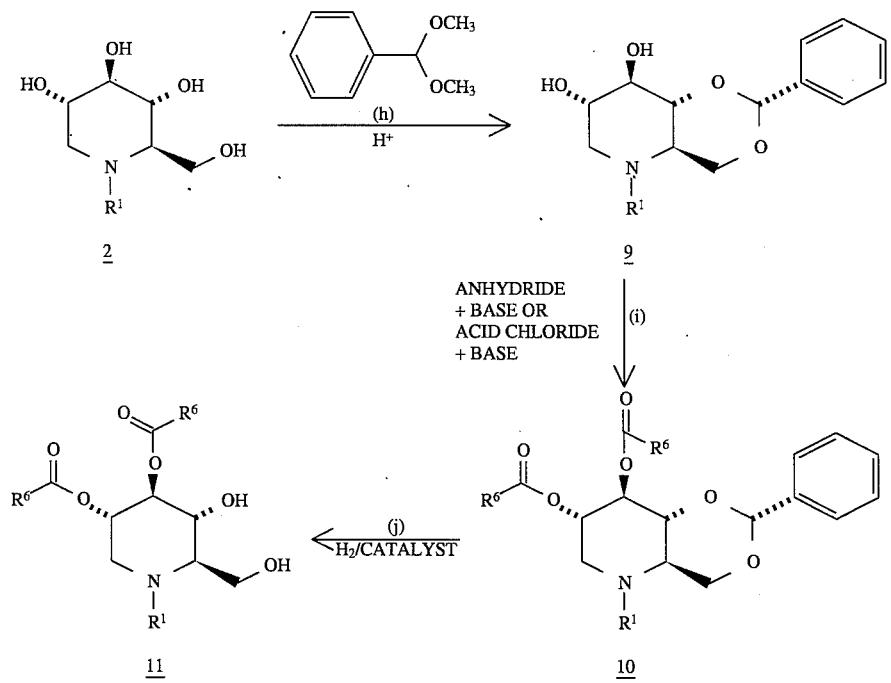

Scheme 1 shows a presently preferred method for making N-substituted, O-acylated DNJ wherein $R^1$ represents N-alkyl or N-aralkyl, and $C(O)R_6$ represents the O-acyl moieties defined hereinbefore, the method involving [step (a)] reductively alkylating DNJ 1 with an alkylaldehyde or arylaldehyde in the presence of hydrogen gas and a catalyst such as palladium/carbon to give N-alkylated DNJ 2, or alternatively alkylating the imino-nitrogen with an alkylhalide or alkyl ester such as an alkyl tosylate, followed by acylation [step (b)] with the carboxylic acid chloride or carboxylic acid anhydride of an alkyl or aralkyl moiety to provide an O-acylated, N-alkyl (or aralkyl) DNJ 3. Suitable alkylaldehydes include but are not limited to butyraldehyde, ethylbutyraldehyde, 2-methylvaleraldehyde, caproaldehyde, and nonylaldehyde. Illustrative arylaldehydes are, e.g., benzaldehyde, ethylbenzaldehyde and hydrocinnamaldehyde. Suitable alkylating agents include, for example, isopropylbromide, tert-butyl tosylate, 3-heptyliodide, alpha-phenethylmesylate and the like. Suitable acid anhydrides include but are not limited to the acetic-, propionic-, butyric-, isobutyric- and benzoic anhydrides.

Scheme 2 shows a presently preferred method for making N-substituted or unsubstituted, optionally O-acylated, DNJ derivatives starting from carbobenzyloxy-protected DNJ. (See, Example 1 herein). In step c, 1,5-(Benzyoxycarbonylimino)-1,5-dideoxy-D-glucitol 4 is acylated as described in step (a) to give the compound 5. Step (d) consists of reductive removal of the carbobenzoxy protecting group by catalytic hydrogenation to give a peracylated DNJ 6. Reductive alkylation (e) of 6 as described above for step (a) gives an N-alkyl, O-acylated DNJ derivative 8. Alternatively, an amide formation reaction (f) with a peracylated DNJ 6 and a carboxylic acid chloride or carboxylic acid anhydride of an alkyl, aryl or aralkyl moiety in the presence of a base provides an N-acylated, O-acylated DNJ derivative 7. The compound 7 can be hydrolyzed with an acid or base to provide the corresponding N-acyl compound 7A. The hydrolysis of the ester groups of 7 without hydrolysis of the amide group may be carried out as is well known to those of ordinary skill in the art with reagents such as sodium hydroxide, sodium methoxide, hydrochloric acid and the like. Reduction of 7 or 7A to provide 2 or 8 (not shown) may be accomplished by using, e.g., lithium aluminum hydride.

Scheme 3 shows a preferred reaction for providing N-substituted, 2,3-O-acylated DNJ deriviatives wherein N-alkyl DNJ 2 is 4-6-O-protected by acetal exchange (h) with dimethoxybenzaldehyde in the presence of acid, followed by acylation (i) and reductive removal of the protecting group (j) essentially as described above for steps (c) and (d), respectively.

Illustrative examples of 1,5-dideoxy-1,5-imino-D-glucitol and their N-alkyl, N-acyl and N-aryl, and optionally O-acylated derivatives are the following:

1,5-(Butylimino)-1,5-dideoxy-D-glucitol, 1,5-(Methylimino)-1,5-dideoxy-D-glucitol, 1,5-(Hexylimino)-1,5-dideoxy-D-glucitol, 1,5-(Nonylylimino)-1,5-dideoxy-D-glucitol, 1,5-(2-Ethylbutylimino)-1,5-dideoxy-D-glucitol, 1,5-(2-Methylpentylimino)-1,5-dideoxy-D-glucitol, 1,5-(Benzyloxycarbonylimino)-1,5-dideoxy-D-glucitol, tetraacetate, 1,5-(Phenylacetylimino)-1,5-dideoxy-D-glucitol, tetraacetate, 1,5-(Benzoylimino)-1,5-dideoxy-D-glucitol, tetraacetate, 1,5-(Butylimino)-1,5-dideoxy-D-glucitol, tetraacetate, 1,5-(Ethyl malonylimino)-1,5-dideoxy-D-glucitol, tetraacetate, 1,5-(Hexylimino)-1,5-dideoxy-D-glucitol, tetraacetate, 1,5-(Nonylimino)-1,5-dideoxy-D-glucitol, tetraacetate, 1,5-(Benzyloxycarbonylimino)-1,5-dideoxy-D-glucitol, tetraisobutyrate, 1,5-(Butylimino)-1,5-dideoxy-D-glucitol, tetrabutyrate, 1,5-(Butylimino)-1,5-dideoxy-D-glucitol, tetrapropionate, 1,5-(Butylimino)-1,5-dideoxy-D-glucitol, tetrabenzoate, 1,5-Dideoxy-1,5-imino-D-glucitol, tetraisobutyrate, 1,5-(Hydrocinnamoylimino)-1,5-dideoxy-D-glucitol, tetraacetate, 1,5-(Methyl malonylimino)-1,5-dideoxy-D-glucitol, tetraacetate, 1,5-(Butylimino)-1,5-dideoxy-D-glucitol, tetraisobutyrate, 1,5-(Butylimino)-1,5-dideoxy-4R,6-O-(phenylmethylene)-D-glucitol, diacetate, 1,5-[(Phenoxymethyl)carbonylimino]-1,5-dideoxy-D-glucitol, tetraacetate, 1,5-[(Ethylbutyl)imino]-1,5-dideoxy-D-glucitol, tetraacetate, 1,5-(Butylimino)-1,5-dideoxy-D-glucitol, 2,3-diacetate, 1,5-(Hexylimino)-1,5-dideoxy-4R,6-O-(phenylmethylene)-D-glucitol, diacetate, 1,5-(Hexylimino)-1,5-dideoxy-D-glucitol, 2,3-diacetate, 1,5-[(2-Methylpentyl)imino]-1,5-dideoxy-D-glucitol, tetraacetate, 1,5-(Butylimino)-1,5-dideoxy-D-glucitol, 6-acetate, 1,5-[(3-Nicotinoyl)imino]-1,5-dideoxy-D-glucitol, tetraacetate, 1,5-(Cinnamoylimino)-1,5-dideoxy-D-glucitol, tetraacetate, 1,5-(Butylimino)-1,5-dideoxy-D-glucitol, 2,3-dibutyrate, 1,5-(Butylimino)-1,5-dideoxy-4R,6-O-(phenylmethylene)-D-glucitol, 2,3-dibutyrate, 1,5-(Phenylacetylimino)-1,5-dideoxy-D-glucitol, tetraisobutyrate, 1,5-[(4-Chlorophenyl)acetylimino]-1,5-dideoxy-D-glucitol, tetraacetate, 1,5-[(4-Biphenyl)acetylimino]-1,5-dideoxy-D-glucitol, tetraacetate, 1,5-(Benzyloxycarbonylimino)-1,5-dideoxy-D-glucitol, tetrabutyrate, and 1,5-Dideoxy-1,5-imino-D-glucitol, tetrabutyrate.

The foregoing compounds can be demonstrated to have inhibitory activity against respiratory syncytial virus in a tetrazolium based cell viability assay. See Example 44.

1,5-dideoxy-1,5-imino-D-glucitol and N-alkyl, N-aralkyl, N-acyl and O-acylated derivatives thereof which have been found to exhibit RSV inhibitor activity, are known to have alpha- and beta-glucosidase inhibitory activity and to inhibit HIV.

The anti-RSV compounds described herein may be used for administration to a mammalian host infected with respiratory syncytial virus by conventional means, preferably in formulation with pharmaceutically acceptable diluents and carriers. The compounds described for use in accordance with the present invention may be used in the free amine form or in their salt form. Pharmaceutically acceptable salt derivatives are illustrated, for example, by the hydrochloride salt.

An "RSV inhibitory effective amount" of a compound disclosed herein is an amount of a disclosed compound which exhibits RSV inhibition, which benefit is not outweighed by adverse toxic effects. An RSV inhibitory effective amount of a 1,5-dideoxy-1,5-imino-D-glucitol or N-alkyl, N-aralkyl, N-acyl and/or O-acylated derivative thereof may be an amount which is from about 0.5 milligrams/kilogram body weight/day to about 750 milligrams/kilogram body weight/day, and may be readily determined by a person of ordinary skill in the art based on in vitro efficacy and/or in vivo effect. Clinical improvement of a patient being treated in accordance with the method of the present invention may be readily determined by an ordinarily skilled clinician, such as by virological testing or by disappearance of clinically characteristic symptoms of RSV infection. A therapeutically effective regimen for treating RSV infection may entail administration of an inhibitory effective amount of an anti-RSV disclosed herein at a rate of 2 to 4 times or more per day for about 7 days to about 14 days or longer. The dosage of an anti-RSV compound which is given and/or the length of treatment time may be increased or decreased based on the type and severity of disease, the age (e.g., pediatric v. adult use) and general health of the patient, and like factors of which a clinician of ordinary skill in the art is aware and utilizes in the management of a patient.

An RSV inhibitor compound as disclosed herein may be administered by oral, intravenous, subcutaneous, intramuscular, intranasal or other conventional route which is employed in the art. Oral administration of an RSV inhibitory compound in the form of a tablet, capsule, syrup, elixir or the like is presently preferred. Suitable formulations of the active compound in combination with pharmaceutically acceptable diluents and carriers in therapeutic dosage form may be readily prepared by reference to general texts in the field of pharmaceutical science such as Remington's Pharmaceutical Sciences, Ed., A. Gennaro, 17th Edition, 1985, Mack Publishing Co., Easton Pa.

The following non-limiting examples further illustrate the invention.

EXAMPLES

Example 1

1,5-(Benzyoxycarbonylimino)-1,5-dideoxy-D-glucitol

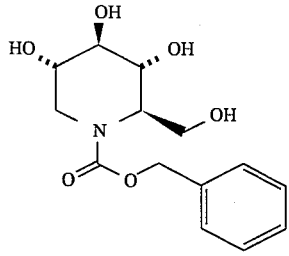

Benzyl chloroformate (1.15 g, 0.00674 mole was added to a solution of 1,5-dideoxy-1,5-imino-D-glucitol (1.0 g, 0.00613 mole), in 50 ml saturated aqueous sodium hydrogen carbonate and stirred for 20 hrs. at room temperature. The product was extracted into ethyl acetate (3×75 ml), dried over anhydrous sodium sulfate, filtered and concentrated in vacuo to an oil. Chromatography on silical gel gave the title compound (1.2 g). Structure assignment was supported by NMR and infrared spectra and by elemental analysis. Analysis calcd. for $C_{14}H_{19}NO_6$: C, 56.56; H, 6.44; N, 4.71. Found: C, 56.29; H, 6.62; N, 4.53.

Example 2

1,5-(Benzyloxycarbonylimino)-1,5-dideoxy-D-glucitol, tetraacetate

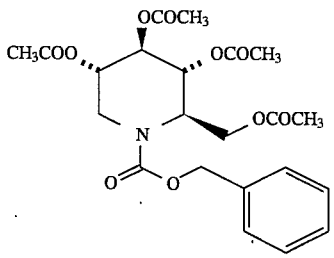

To a solution of the title product of Example 1 (491 mg, 1.65 moles) in 5 ml of pyridine was added 2 ml of acetic anhydride. The resulting mixture was stirred for 15 minutes at room temperature and then at reflux for 5 minutes. After cooling, the mixture was poured into 25 ml of ice water and extracted with three portions of ethyl acetate. The combined organic extracts were washed with dilute hydrochloric acid, dried over sodium sulfate, filtered, and the solvent removed on a rotary evaporator. Chromatography on silica gel using a gradient of 25 to 100% ethyl acetate-hexane as eluant gave the title compound (510 mg) as an oil. Analysis for $C_{22}H_{27}NO_{10}$ (MW 465.46): Calcd. C, 56.76; H, 5.85; N, 3.01. Found: C, 56.72; H, 5.82; N, 3.02.

Example 3

1,5-Dideoxy-1,5-imino-D-glucitol, tetraacetate

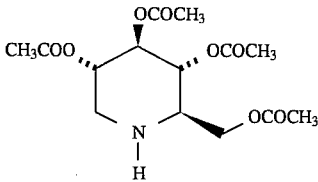

The title compound of Example 2 (13.417 g, 0.029 moles) was hydrogenated (5 psi, room temperature 2 hrs.) in 250 ml of methanol containing 4% Pd/C (3.0 g). This mixture was filtered and concentrated in vacuo to give an oil. Chromatography on silica gel gave the title compound as a waxy solid. Structure assignment was supported by NMR, infrared spectra and elemental analysis. Analysis calcd. for $C_{14}H_{21}NO_8$: C, 50.75; H, 6.39; N, 4.23. Found: C, 50.53; H, 6.41; N, 4.14.

Example 4

1,5-(Phenylacetylimino)-1,5-dideoxy-D-glucitol-tetraacetate

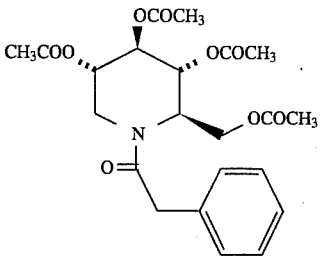

Phenylacetyl chloride (0.23 g, 0.0015 mole) was added to a cold (−76° C., solution of the title compound of Example 3 (0.5 g, 0.0015 mole) in 30 ml tetrahydrofuran. Triethylamine (0.5 ml) was added and the solution stirred for 20 hrs at room temperature. Triethylamine hydrochloride was removed by filtration and the filtrate concentrated in vacuo to give 0.81 g of an oil. Chromatography on silica gel and recrystallizing from ethyl acetate/hexane gave the title product, m.p. 98°–100° C. Structure assignment was supported by NMR, infrared spectra and elemental analysis. Analysis calcd. for $C_{22}H_{27}NO_9$: C, 58.79; H, 6.05; N, 3.12. Found: C, 58.74; H, 6.12; N, 3.14.

Example 5

1,5-(Benzoylimino)-1,5-dideoxy-D-glucitol, tetraacetate

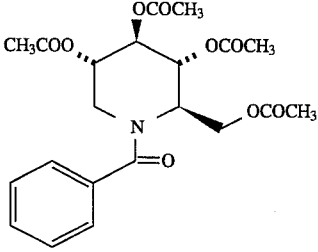

The title compound, m.p. ca. 138° C., was prepared by the method of Example 4 using benzoyl chloride instead of phenylacetyl chloride. Structure assignment was supported by NMR, infrared spectra and elemental analysis. Analysis calcd. for $C_{21}H_{25}NO_9$: C, 57.93; H 5.79; N, 3.22. Found: C, 57.88; H, 5.82; N, 3.30.

Example 6

1,5-(Butylimino)-1,5-dideoxy-D-glucitol

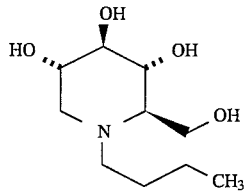

A solution of 1,5-dideoxy-1,5-imino-D-glucitol (5.14 g, 0.0315 mole), butyraldehyde (3.35 ml, 0.0380 mole) and Pd black (1 g) in 200 ml methanol was hydrogenated (60 psi/29° C./21 hrs.). After filtering the resulting mixture, the filtrate was concentrated in vacuo to an oil. The title compound was crystallized from acetone and recrystallized from methanol/acetone, m.p. ca. 132° C. Structure assignment was supported by NMR, infrared spectra and elemental analysis. Analysis calcd. for $C_{10}H_{21}NO_4$: H, 9.65; N, 6.39. Found: C, 54.46; H, 9.33; N, 6.46.

Example 7

1,5-(Butylimino)-1,5-dideoxy-D-glucitol, tetraacetate

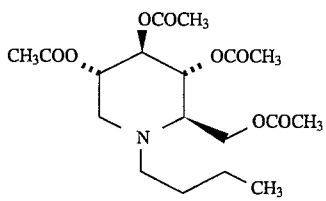

Acetic anhydride (1.08 g, 0.0106 mole) was added to the title compound of Example 6 (0.50 g, 0.0023 mole) in 5 ml pyridine and stirred for 17 days at room temperature. The product was evaporated under nitrogen gas. The resulting title compound was purified by silica gel chromatography. Structure assignment was supported by NMR, infrared spectra and elemental analysis. Analysis calcd. for $C_{18}H_{29}No_8$: H, 7.54; N, 3.62. Found: C, 55.42; H, 7.50; N, 3.72.

Example 8

1,5-(Ethyl malonylimino)-1,5-dideoxy-D-glucitol, tetraacetate

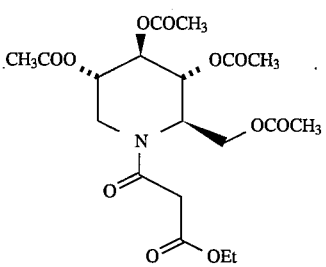

Ethyl malonyl chloride (0.5 g, 0.0033 mole) in 10 ml tetrahydrofuran was added to a cold (0o C.) solution of the title compound of Example 3 (1.0 g, 0.0030 mole) in 30 ml tetrahydrofuran. After stirring for 30 min. a solution of triethylamine (0.67 g, 0.0066 mole) in 10 ml tetrahydrofuran was added. The mixture was allowed to come to room temperature and stirred for 20 hrs. Triethylamine hydrochloride was removed by filtration and the filtrate concentrated in vacuo to give an oil. Chromatography on silica gel gave the title compound as a clear oil. Structure assignment was supported by NMR, infrared spectra and elemental analysis. Analysis calcd. for $C_{19}H_{27}No_{11}$: C, 51.23; H, 6.11; N, 3.14. Found: C, 50.99; H, 6.14; N, 3.13.

Example 9

1,5-(Methylimino)-1,5-dideoxy-D-glucitol

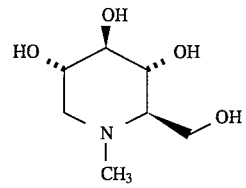

A solution of 1,5-dideoxy-1,5-imino-D-glucitol (7.5 g, 0.046 mole), formaldehyde (37%, 26.0 g, 0.322 mole) and 5% Palladium black in 300 ml methanol was hydrogenated (60 psi/25° C./20 hrs). After filtering the resulting mixture, the filtrate was concentrated to give a foam. The product was crystallized from methanol-acetone to give a white solid. Structure assignment was supported by NMR, infrared spectra and elemental analysis. Analysis calcd. for $C_7H_{15}NO_4$, C 47.45; H, 8.53; N, 7.91. Found: C, 47.24; H, 8.66; N, 7.83.

Example 10

1,5-(Methylimino)-1,5-dideoxy-D-glucitol, tetraacetate

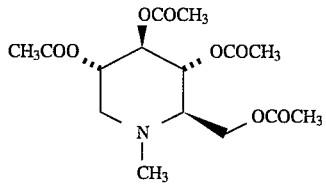

Acetic anhydride (0.69 g, 0.0068 mole) was added to the title compound of Example 9 (0.20 g, 0.0011 mole) in 10 ml pyridine and stirred at room temperature for 5 days. The product was concentrated with a gentle flow of nitrogen gas. The residue was dissolved in 25 ml ethyl acetate, washed with water, dried over sodium sulfate, filtered and concentrated to an oil. The product was purified by silica gel chromatography and recrystallized from ethyl acetate-hexane (m.p. 102° C.). Structure assignment was supported by NMR, infrared spectra and elemental analysis. Analysis calcd. for $C_{12}H_{23}NO_8$: C, 52.17; H, 6.71; N, 4.06. Found: C, 52.15; H, 6.72; N, 3.97.

Example 11

1,5-(Hexylimino)-1,5-dideoxy-D-glucitol

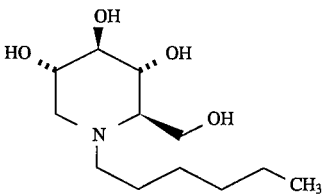

A mixture of 1,5-dideoxy-1,5-imino-D-glucitol (0.5 g, 0.0031 moles), caproaldehyde (0.45 g, 0.0045 mole) and 5% Palladium black (0.1 g) in methanol (105 ml) was hydrogenated (5 psi/25° C./5 days). After filtering the resulting mixture, the filtrate was concentrated with a flow of nitrogen to give an oily solid. The title compound was crystallized from acetone-ethanol, DSC ca. 115° C. Structure assignment was supported by NMR, infrared spectra and elemental analysis. Analysis calcd. for $C_{12}H_{25}NO_4$: C, 58.27; H, 10.19; N, ; 5.66. Found: C, 58.19; H, 10.24; N, 5.65.

Example 12

1,5-(Hexylimino)-1,5-dideoxy-D-glucitol, tetraacetate

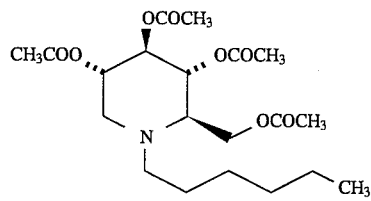

The title compound was prepared by the Method of Example 10 utilizing the product of Example 11 instead of 1,5-(methylimino)-1,5-dideoxy-D-glucitol. The structure assignment was supported by NMR, infrared spectra and elemental analysis. Analysis calcd. for $C_{20}H_{33}NO_8$: C, 57.82; H, 8.01; N, 3.37. Found: C, 57.73; H, 7.83; N, 3.36.

Example 13

1,5-(Nonylimino)-1,5-dideoxy-D-glucitol

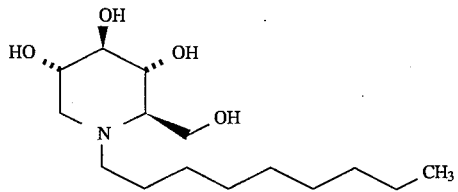

A solution of 1,5-dideoxy-1,5-imino-D-glucitol (0.5 g, 0.0031 mole); nonyl aldehyde (0.52 g, 0.0037 mole) and 5% Pd black (0.1 g) in methanol (100 ml) was hydrogenated (60 psi/25° C./46 hrs.). After filtering the resulting mixture, the filtrate was concentrated with a gentle flow of nitrogen to an oily solid. This material was stirred with a small amount of acetone and the solid filtered. Recrystallization from ethanol-acetone gave the title compound, DSC ca. 109° C. Structure assignment was supported by NMR, infrared spectra and elemental analysis.

Analysis calcd. for $C_{15}H_{31}NO_4$: C, 62.25; H, 10.80; N, 4.84. Found: C, 62.15; H, 10.86; N, 4.79.

Example 14

1,5-(Nonylimino)-1,5-dideoxy-D-glucitol, tetraacetate

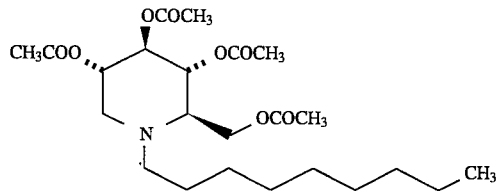

The title compound was prepared by the Method of Example 10 utilizing the product of Example 13 instead of 1,5-(methylimino)-1,5-dideoxy-D-glucitol. The structure assignment was supported by NMR, infrared spectra and elemental analysis. Analysis calcd. for $C_{23}H_{39}NO_8$: C, 60.37; H, 8.59; N, 3.06. Found: C, 60.19; H, 7.99; N, 3.12.

Example 15

1,5-(Benzyloxlycarbonylimino)-1,5-dideoxy-D-glucitol, tetraisobutyrate

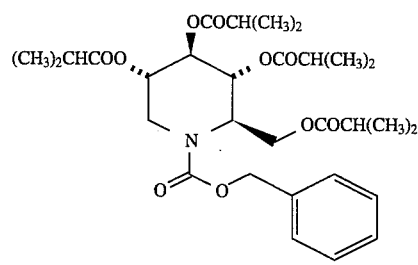

To a solution of the title product of Example 1 (2.0 g, 0.0067 mole) in 30 ml pyridine was added isobutyric anhydride (6.4 g, 0.0436 mole) and stirred at room temperature for 6 days. The reaction was poured into 150 ml water, stirred for 20 hrs. and extracted with two portions of ethyl acetate (2×100 ml). The combined organic extracts were washed with water (4×75 ml), dried over sodium sulfate, filtered, and the solvent removed on a rotary evaporator to give an oil. The title compound was purified by silica gel chromatography. The structure assignment was supported by NMR, infrared spectra and elemental analysis. Analysis calcd. for $C_{30}H_{43}NO_{10}$: C, 62.38; H, 7.50; N, 2.42. Found: C, 62.23; H, 7.60; N, 2.44.

Example 16

1,5-(Butylimino)-1,5-dideoxy-D-glucitol, tetrabutyrate

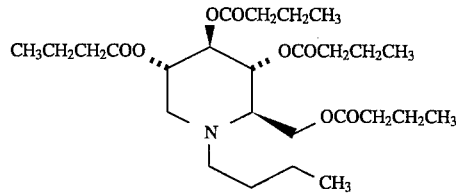

The title compound was prepared by the Method of Example 7 using n-butyric anhydride instead of acetic anhydride. After purification by silica gel chromatography the product was crystallized from pentane. The structure assignment was supported by NMR, infrared spectra and elemental analysis. Analysis calcd. for $C_{22}H_{45}NO_8$: C, 62.50; H, 9.08; N, 2.80. Found: C, 62.48; H, 9.12; N, 2.84.

Example 17

1,5-(Butylimino)-1,5-dideoxy-D-glucitol, tetrapropionate

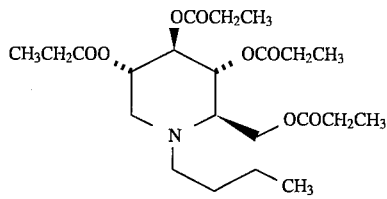

The title compound was prepared by the Method of Example 7 substituting propionic anhydride for acetic anhydride. The structure was supported by NMR, infrared spectra and elemental analysis. Analysis calcd. for $C_{22}H_{37}NO_8$: C, 59.58; H, 8.41; N, 3.16. Found: C, 59.56; H, 8.68; N, 3.19.

Example 18

1,5-(Butylimino)-1,5-dideoxy-D-glucitol, tetrabenzoate

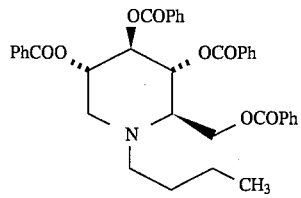

The title compound was prepared by the Method of Example 7 substituting benzoic anhydride for acetic anhydride. The reaction was allowed to stir at room temperature for 27 days. The structure assignment was supported by NMR, infrared spectra and elemental analysis.

Analysis calcd. for $C_{38}H_{37}NO_8$: C, 71.80; H, 5.87; N, 2.20. Found: C, 71.49; H, 5.92; N, 2.24.

Example 19

1,5-Dideoxy-1,5-imino-D-glucitol, tetraisobutyrate

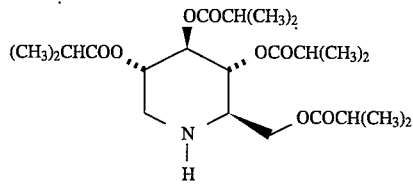

The title compound of Example 15 (2.65 g, 0.0046 mole) was hydrogenated (15 psi, room temperature, 4 hr.) in 100 ml methanol containing 5% Pd/C. This mixture was filtered and concentrated by a rotary evaporator to a solid which was recrystallized from ethyl acetate-hexane (DSC 63° C.). Assignment was supported by NMR, infrared spectra and elemental analysis. Analysis calcd. for $C_{22}H_{37}NO_8$: C, 59.58; H, 8.41; N, 3.16. Found: C, 59.49; H, 8.46; N, 3.17.

Example 20

1,5-(Hydrocinnamoylimino)-1,5-dideoxy-D-glucitol, tetraacetate

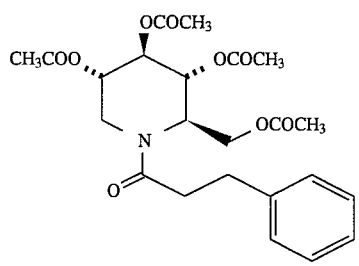

By the method of Example 4 and substituting hydrocinnamoyl chloride for phenylacetyl chloride the title compound was prepared Structure assignment was supported by NMR, infrared spectra and elemental analysis.

Analysis calcd. for $C_{23}H_{29}NO_9$: C, 59.60; H, 6.31; N, 3.02. Found: C, 59.49; H, 6.25; N, 3.08.

Example 21

1,5-(Methyl malonylimino)-1,5-dideoxy-D-glucitol, tetraacetate

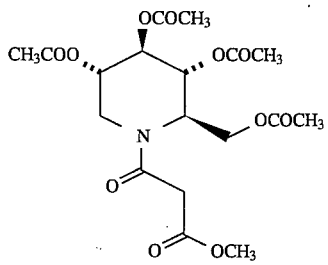

The title compound was prepared by the Method of Example 8 and substituting methyl malonyl chloride for ethyl malonyl chloride. The structure assignment was supported by NMR, infrared spectra and elemental analysis.

Analysis calcd. for $C_{18}H_{25}NO_{11}$: C, 50.12; H, 5.84; N, 3.25. Found: C, 49.91; H, 5.82; N, 3.13.

Example 22

1,5-(Butylimino)-1,5-dideoxy-D-glucitol, tetraisobutyrate

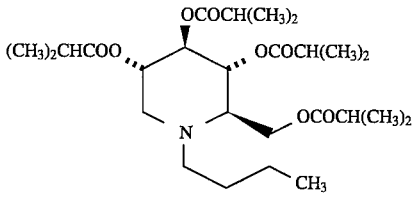

The title compound was prepared by the Method of Example 7 and substituting isobutyric anhydride for acetic anhydride, m.p. 59° C. The structure was supported by NMR, infrared spectra and elemental analysis. Analysis calcd. for $C_{26}H_{45}NO_8$: C, 62.50; H, 9.08; N, 2.80. Found: C, 62.43; H, 9.24; N, 2.82.

Example 23

1,5-(Butylimino)-1,5-dideoxy-4R, 6-0-(phenylmethylene)-D-glucitol

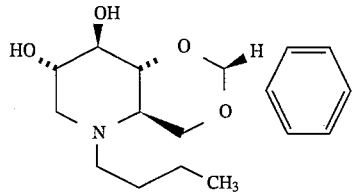

p-Toluenesulfonic acid monohydrate (10.4 g, 0.055 mole) was added to a solution of dimethoxytoluene (20.8 g, 0.137 mole) in 150 ml of dimethylformamide. After stirring for 3.5 hrs, 1,5-(butylimino)-1,5-dideoxy-D-glucitol (10.0 g, 0.046 mole) was added and the solution was stirred at room temperature for 18 days. The reaction was concentrated on a rotary evaporator. The residue was passed through a column containing Amberlite IRA-400 ion exchange resin with methanol. The eluant was concentrated to a brown oil. The title compound was purified by silica gel chromatography and crystallized from ethyl acetate-hexane (DSC 118° C.). The structure assignment was supported by NMR, infrared spectra and elemental analysis.

Analysis calcd. for $C_{17}H_{25}NO_4$: C, 66.43; H, 8.20; N 4.56. Found: C, 66.38; H, 8.20; N, 4.52.

Example 24

1,5-(Butylimino)-1,5-dideoxy-4R, 6-0-(phenylmethylene)-D-glucitol, diacetate

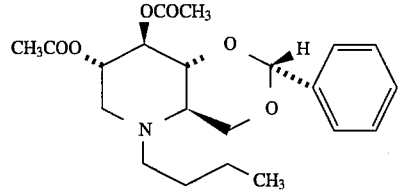

Acetic anhydride (0.30 g, 0.0029 mole) was added to the product of Example 23 (0.30 g, 0.001 mole) in 10 ml pyridine and stirred for 5 days at room temperature. Water (5 ml) was added and the solution stirred for 1 hr. After removal of the solvent by a rotary evaporator, the product was purified by silica gel chromatography and recrystallized from ethyl acetate-hexane (DSC 126° C.). Structure assignment was supported by NMR, infrared spectra and elemental analysis. Analysis calcd. for $C_{21}H_{29}NO_6$: C, 64.43; H, 7.47; N, 3.58. Found: C, 64.39; H, 7.70; N, 3.53.

Example 25

1,5-[(Phenoxymethyl)carbonylimino]-1,5-dideoxy-D-glucitol, tetraacetate

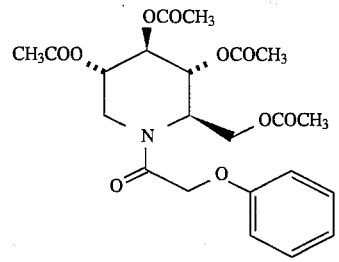

The title compound was prepared by the Method of Example 4 and substituting phenoxyacetyl chloride for phenylacetyl chloride (DSC, 219° C.). Structure assignment was supported by NMR, infrared spectra and elemental analysis. Analysis calcd. for $C_{22}H_{27}NO_{10}$: C, 56.77; H, 5.85; N, 3.01. Found: C, 56.81; H, 5.83; N, 3.21.

Example 26

1,5-[(2-Ethylbutyl)imino]-1,5-dideoxy-D-glucitol

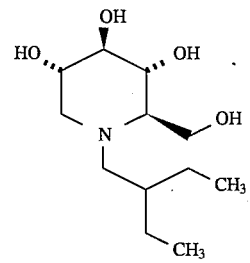

A solution of 1,5-dideoxy-1,5-imino-D-glucitol (0.99 g, 0.0061 mole), 2-ethylbutyraldehyde (0.98 g, 0.0098 mole) and 5% Pd black in methanol (68 ml), tetrahydrofuran (34 ml) and water (17 ml) was hydrogenated (5 psi/25° C./72 hrs.). After filtering the resulting mixture, the filtrate was concentrated to an oily solid. This residue was dissolved in methanol (40 ml) and cooled. The white solid was removed by filtration to give as 1,5-dideoxy-1,5-imino-D-glucitol. The filtrate was concentrated to an oil. The product was purified by silica gel chromatography to give a white solid. Recrystallization from methanol-ethyl acetate gave the title compound, DSC ca. 95° C. Structural assignment was supported by NMR, infrared spectra and elemental analysis.

Analysis calcd. for $C_{12}H_{25}NO_4$: C, 58.27; H, 10.19; N, 5.66. Found: C, 57.89; H, 10.09; N, 5.69.

Example 27

1,5-[(2-Ethylbutyl)imino]-1,5-dideoxy-D-glucitol, tetraacetate

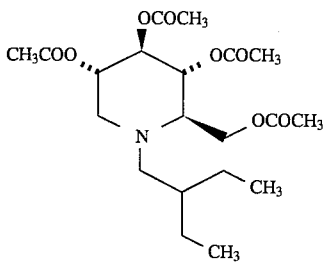

The title compound was prepared by the Method of Example 7 and substituting 1,5-[(2-ethylbutyl)imino]-1,5-dideoxy-D-glucitol for 1,5-(butylimino)-1,5-dideoxy-D-glucitol. Structure assignment was supported by NMR, infrared spectra and elemental analysis. Analysis calcd. for $C_{20}H_{33}NO_8$: C, 57.82; H, 8.01; N, 3.37. Found: C, 57.42; H, 7.92; N, 3.31.

Example 28

1,5-(Butylimino)-1,5-dideoxy-D-glucitol, 2,3-diacetate

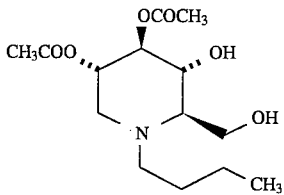

A mixture of the title compound of Example 24 (1.9 g, 0.0049 mole) and 20% Pd black (2.0 g) in methanol, tetrahydrofuran and methanol (6:4:2) was hydrogenated (60 psi/60° C./21 hr.). After filtering the resulting mixture, the filtrate was concentrated in vacuo to an oil. The product was purified by silica gel chromatography. Structure assignment was supported by NMR and elemental analysis. Analysis calcd. for $C_{14}H_{25}NO_6$: C, 55.43; H, 8.31; N, 4.62. Found: C, 55.40; H, 8.38; N, 4.50.

Example 29

1,5-(Hexylimino)-1,5-dideoxy-4R,6-O-(phenylmethylene)-D-glucitol

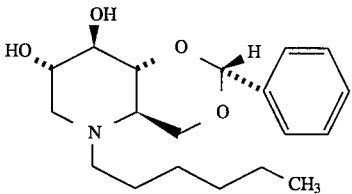

The title compound was prepared by the Method of Example 23 and substituting the product of Example 11 for 1,5-(butylimino)-1,5-dideoxy-D-glucitol (DSC 101° C.) Structure assignment was supported by NMR, infrared spectra and elemental analysis. Analysis calcd. for $C_{19}H_{29}NO_4$: C, 68.03; H, 8.71; N, 4.18. Found: C, 68.04; H, 8.76; N, 4.15.

Example 30

1,5-(Hexylimino)-1,5-dideoxy-4R,6-O-(phenylmethylene)-D-glucitol, 2,3-diacetate

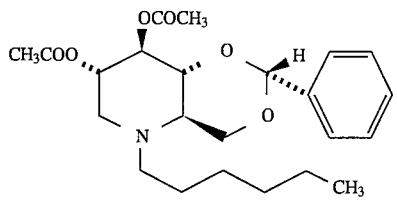

The title compound can be prepared by the Method of Example 24 and substituting the product of Example 29 for the product of Example 23.

Example 31

1,5-(Hexylimino)-1,5-dideoxy-D-glucitol, 2,3-diacetate

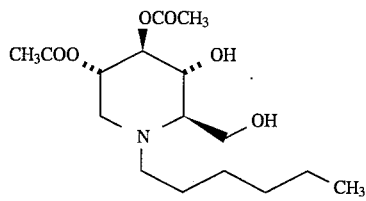

The title compound can be prepared by the Method of Example 28 by substituting the product of Example 30 for the product of Example 24 in the synthesis reaction.

Example 32

1,5-[(2-Methylpentyl)imino]-1,5-dideoxy-D-glucitol

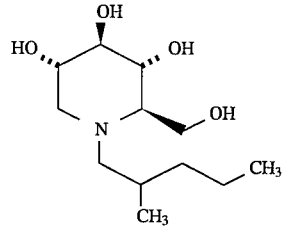

The title compound was prepared as a solid by the Method of Example 26 by using 2-methylvaleraldehyde instead of 2-ethylbutyraldehyde in the synthesis reaction. (DSC ca. 89° C.) The structure was supported by NMR; infrared spectra and mass spectroscopy.

Example 33

1,5-[(2-Methylpentyl)imino]-1,5-dideoxy-D-glucitol, tetraacetate

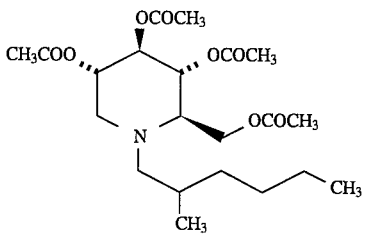

The title compound was prepared by the Method of Example 7 by substituting 1,5-[(2-Methylpentyl)imino]-1,5-dideoxy-D-glucitol for 1,5-(butylimino)-1,5-dideoxy-D-glucitol in the synthesis reaction. The structure assignment was supported by CMR and NMR.

Example 34

1,5-(Butylimino)-1,5-dideoxy-D-glucitol, 6-acetate

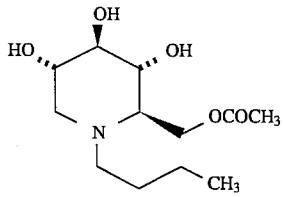

Acetic anhydride (0.46 g, 0.0046 mole) was added to the title compound of Example 6 (1.0 g, 0.0046 mole) in 150 ml pyridine cooled to –40° C. by a dry ice/acetone bath. The reaction was allowed to come to room temperature and stirred for 20 hrs. Water (5 ml) was added and the reaction stirred for 1 hr. The solution was concentrated in vacuo to an oil. The title compound was purified by silica gel chromatography to give a solid which was recrystallized from methanol-ethyl acetate (DSC 131° C.). The structure assignment was supported by NMR, mass spectroscopy and elemental analysis. Analysis calcd. for $C_{12}H_{23}NO_5$—⅓ $H_2O$: C, 54.04; H, 8.92; N, 5.25. Found: C, 53.97; H, 9.04; N, 5.53.

Example 35

1,5-[(3-Nicotinoyl)imino]-1,5-dideoxy-D-glucitol, tetraacetate

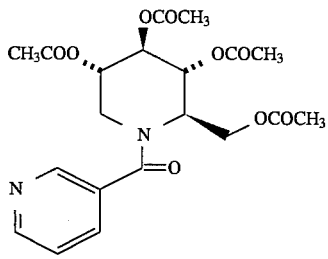

The title compound was prepared by the Method of Example 4 by substituting nicotinoyl chloride for phenylacetyl chloride in the synthesis reaction. Structure assignment was supported by NMR.

Example 36

1,5-(Cinnamoylimino)-1,5-dideoxy-D-glucitol, tetraacetate

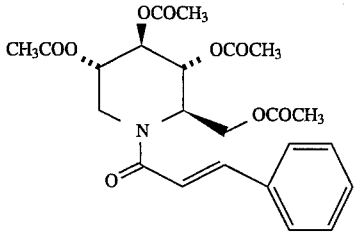

Triethylamine (0.5 ml) was added to a cold (0° C.) solution of 1,5-dideoxy-1,5-imino-D-glucitol (0.5 g, 0.0015 mole) and cinnamoyl chloride (0.25 g, 0.0015 mole) in 50 ml tetrahydrofuran. The mixture was allowed to come to room temperature and stirred for 3 days. The reaction mixture was concentrated in vacuo to an oily solid. Ethyl acetate was added to the residue and the solid removed by filtration. After concentrating the filtrate in vacuo, the title compound was purified by silica gel chromatography. The structure assignment was supported by NMR, infrared spectra and elemental analysis. Analysis calcd. for $C_{23}H_{27}NQ_9$: C, 59.86; H, 5.90; N, 3.04. Found: C, 59.66; H, 5.93; N, 2.99.

Example 37

1,5-(Butylimino)-1,5-dideoxy-4R,6-O-(phenylmethylene)-D-glucitol, 2,3-dibutyrate

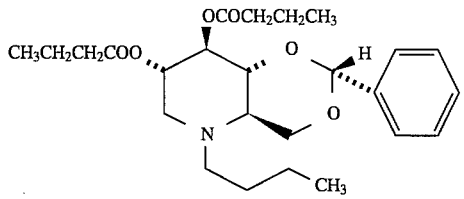

The title compound was prepared by the Method of Example 24 by substituting butyric anhydride for acetic anhydride in the synthesis reaction. The structure assignment was supported by NMR, infrared spectra and elemental analysis. Analysis calcd. for $C_{25}H_{37}NO_6$: C, 67.09; H, 8.33; N, 3.13. Found: C, 67.05; H, 8.44; N, 3.12.

Example 38

1,5-(Butylimino)-1,5-dideoxy-D-glucitol, 2,3-dibutyrate

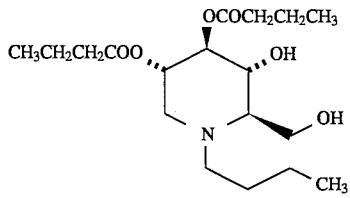

The title compound was prepared by the Method of Example 28 by substituting the title compound of Example 37 for the title compound of Example 24. Structure assignment was supported by NMR and elemental analysis.

Analysis calcd. for $C_{18}H_{33}NO_6$: C, 60.14; H, 9.25; N, 3.90. Found: C, 59.98; H, 9.38; N, 3.82.

Example 39

1,5-(Phenylacetylimino)-1,5-dideoxy-D-glucitol, tetraisobutyrate

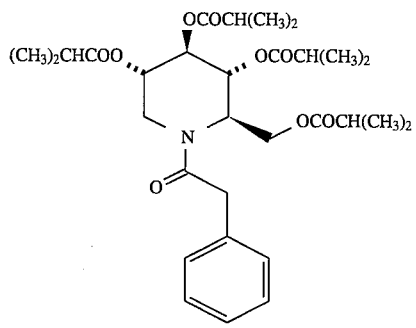

The title compound was prepared by the Method of Example 4 by substituting the title product of Example 19 for the title product of Example 3 in the synthesis reaction. (DSC 96° C., from ethyl acetatehexane.) The structure assignment was supported by NMR, infrared spectra and elemental analysis. Analysis calcd. for $C_{30}H_{43}NO_9$: C, 64.15; H, 7.72; N, 2.49. Found: C, 64.15; H, 7.77; N, 2.30.

Example 40

1,5-[(4-Chlorophenyl)acetylimino]-1,5-dideoxy-D-glucitol, tetraacetate

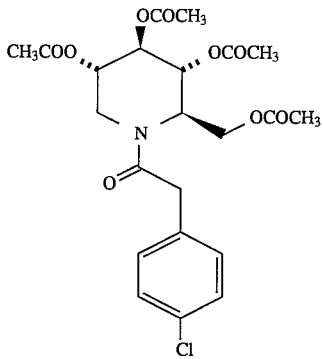

The title compound was prepared by the Method of Example 4 by substituting para-chlorophenylacetyl chloride for phenylacetyl chloride in the synthesis reaction. The structure assignment was supported by NMR, infrared spectra and elemental analysis. Analysis calcd. for $C_{22}H_{26}ClNO_9$: C, 54.61; H, 5.42; $C_{1, 7.33}$; N, 2.89. Found: C, 54.61; H, 5.45; $C_{1, 7.35}$; N, 2.88.

Example 41

1,5-(Benzyloxycarbonylimino)-1,5-dideoxy-D-glucitol, tetrabutyrate

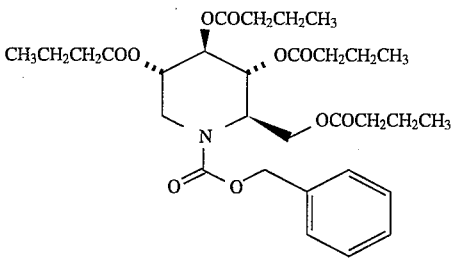

The title compound was prepared by the Method of Example 15 by substituting butyric anhydride for isobutyric anhydride in the synthesis reaction. The structure assignment was supported by NMR, infrared spectra and elemental analysis. Analysis calcd. for $C_{30}H_{43}NO_{10}$: C, 62.38; H, 7.50; N, 2.42. Found: C, 62.21; H, 7.52; N, 2.42.

Example 42

1,5-Dideoxy-1,5-imino-D-glucitol, tetrabutyrate

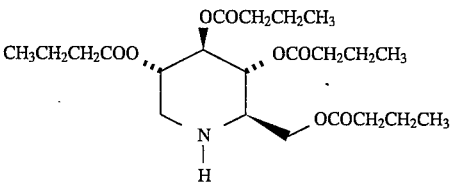

The title compound was prepared by the Method of Example 19 and substituting the product of Example 41 for the product of Example 15. The structure assignment was supported by NMR infrared spectra and elemental analysis.
Analysis calcd. for $C_{22}H_{37}NO_8$: C, 59.58; H, 8.41; N, 3.16. Found: C, 59.46; H, 8.52; N, 3.19.

Example 43

1,5-(3-Phenylpropylimino)-1,5-dideoxy-D-glucitol

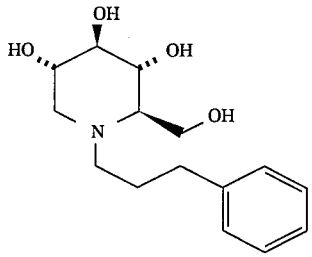

The title compound was prepared by the method of Example 6 and substituting hydrocinnamaldehyde for butyraldehyde. The structure assignment was supported by NMR, infrared spectra and elemental analysis. Analysis calcd. for $C_{15}H_{23}NO_4$: C, 64.04; H, 8.24; N, 4.98. Found C, 63.66; H, 8.16; N, 4.93.

Example 44

Respiratory Syncytial Virus Assay

This example describes a tetrazolium-based cell viability assay and demonstrates the anti-RSV activity of various compounds which were prepared as described above.

The tetrazolium based cell viability assay is based upon the ability of mitochondrial dehydrogenase which is present in viable cells to catalyze the reduction of a yellow tetrazolium salt known as MTT [3-(4,5-dimethylthiazol-2-yl)-2, 5-diphenylthtiazolium bromide] to a dark blue/purple formazon product, generally as described by K. Rubino et al., J. Virological Methods, 39, 55–67 (1992)

Formazan is only slightly soluble in aqueous solutions, and therefore appears as dark cell-associated crystals. The crystals may be readily solublized in an organic solvent and the absorbance of the resulting blue/purple solution may be quantified using a multi-well plate spectrophotometer. The absorbance values obtained by the method described below have been found to be directly proportional to the number of viable cells present.

RSV infection results in a marked reduction in cell viability and thus a lowered rate of formazan production. The assay method gives a very low absorbance value (practically zero) in wells which contain virus-infected cells and no compound or a compound which lacks anti-RSV activity. Compounds which inhibit RSV replication should prevent cell death and will therefore result in an increased intensity of color of the formazan solution. The measurement of viral growth as a function of cell viability allows the assay to be used for establishing levels of compound cytotoxicity in uninfected cells within the same assay. Thus, the assay provides a rapid colorimetric method for measuring RSV specific cytopathic effect.

The HEp-2 cells and RSV strain A2 virus which are used in the assay are publicly available and were obtained from the American Tissue Culture Collection. HEp-2 cells correspond to ATCC accession no. CCL32; and Respiratory Syncytial Virus, strain A2 corresponds to ATCC accession no. VR-1302. Respiratory syncytial virus was grown (i.e., multiplied) and titered in HEp-2 cells.

The RSV inhibition assay was carried out as follows. The assay was performed in 96 well microtiter plates seeded with $2.5 \times 10^4$ cells per well. To provide a sufficient number of cells to seed the plates, stock cultures of HEp-2 cells were first grown in tissue culture flasks to about 80–100% confluency. The cell layer was washed with room temperature PBS (without calcium and magnesium) and then trypsinized (JRH Biosciences cat. #59-22877P) in a minimal volume of trypsin solution at 37° C. to detach them from the growth surface. Detached cells were resuspended and carefully dispersed in Minimal Essential Medium (MEM) (JRH Biosciences cat. #210-3510) containing 2% FBS (fetal bovine serum) and the concentration of viable cells was determined by trypan blue exclusion. Cell density was adjusted to $2.5 \times 10^5$ viable cells/ml by further dilution in MEM+2% FBS.

Test compound(s) and positive control (ribavirin) were added and serially diluted in the microtiter plate to the desired concentrations (8 replicates/compound/concentration plus 8 control wells/plate which received no compound).

The cell suspension was divided into a first portion to which respiratory syncytial virus (RSV A2) was added at a multiplicity of infection of 1, and a second portion to which no virus was added. The virus-infected cell suspension was mixed by low speed vortexing and 100 µl of the virus-infected cell suspension was immediately added to half of the wells in the 96 well plate (corresponding to 4 replicates of each compound dilution). 100 µl of the virus-free cell suspension was added to the other half of the wells in the microtiter plate (corresponding to the other 4 replicates for each compound and dilution). A multiplicity of infection equal to 1 was selected based on the observation this concentration of virus is just sufficient to produce a cytopathic effect that essentially eliminated MTT metabolism in infected, untreated cells during the time course of the assay (determined previously by a viral dilution assay).

The plates were incubated at 37° C., 5% $CO_2$ for 5 to 6 days.

After the incubation period, MTT (Sigma Chemical Co., St. Louis, Mo., Cat. #M2128) was dissolved in serum free MEM to give a 3 mg/ml solution and 100 µl of MTT solution was added to each well and the plates further incubated for 2 hours at 37° C. The reaction was stopped by aspiration of the media to chemical waste, being careful not to remove the formazan crystals, and 200 µl of isopropanol was added to the wells to dissolve the crystals. The optical density of the formazan/isopropanol solution from each well was determined using a Dynatech MR5000 multiplate reader at 570 nm with a 630 nm reference. The multiplate reader was connected to a computer which received and stored the optical density values on a file server such that the optical density values could be later calculated.

The optical density obtained for each of the four replicate wells per assay condition were averaged and used in the following formula derived by N-Ayisi et al., J. Virological Methods, 33, 335–344 (1991), to calculate the cell protection values for each compound/concentration. The % cell protection values and % cytotoxicity values were in turn used to calculate the $EC_{50}$ and $CC_{50}$ values.

$$\% \text{ Cell Protection} = 1 + \left[ \frac{(ODT)RSV - (ODT)mock}{(ODC)mock - (ODC)RSV} \right] \times 100$$

$$\% \text{ Cytotoxicity} = 100 - \left[ \left[ \frac{(ODT)mock}{(ODC)mock} \right] \times 100 \right]$$

Where (ODT)RSV=optical density in the presence of virus and compound (ODT)mock=optical density in the absence of virus, but in the presence of compound (ODC)mock=optical density in the absence of virus and in the absence of compound (ODC)RSV=optical density in the presence of virus, but in the absence of compound The $EC_{50}$ values were calculated from the % cell protection values obtained. The CC50 values were calculated from the % cytotoxicity values obtained. The data was best fit to a curve using an adaptation of the Levenberg-Marquardt method of least squares minimization as explained in the book Numerical Recipes in C (Second Edition) by Cambridge University Press, in chapter 15, page 683 in accordance with the following algorithm:

$$y = (D-A)/(1+\exp(B*C - B* \ln(x)))$$

where:
  y=dependent variable (biological response)
  x=independent variable (concentration of compound tested)
  A=minimum value of assay
  B="slope"
  C=ln(EC$_{50}$) (or ln(CC50))
  D=maximum value of assay
  * represents multiplication.

The nonlinear regression routine used allows for weighted adjustments based on standard deviation of each observed data value. However, this implementation assumes that data errors are normally distributed uniformly across the range of the observed values, so the array of sigmas are just set to 1.0's to effectively remove the weighing.

To fit the data to a curve so as to obtain EC50 and CC50 values, first A is set to equal a value which is 0.99 * the minimum observed assay value; D is set to equal 1.01 * the maximum observed assay value; slope (B) is calculated by applying the LINEST Excel function (Microsoft Excel Version 4.0, function reference p.254, Microsoft Corporation, Redmond, Wash.) to the sets of predicted values and predicted concentrations; and C, the ln(EC50), equals the Y-intercept calculated by applying the LINEST Excel function to the sets of predicted values and predicted concentrations. In the event that the obtained results show D or A to differ significantly from 100% or 0% respectively, curve fits were repeated with the value for D fixed to 100% and/or the value of A fixed to 0%, in which case the program calculates only the slope and the ln(EC50) values using the fixed minimum and maximum provided.

The predicted values are calculated as follows:

$$\frac{\min + (\max - \min)}{(1 + \exp(\text{slope} * \ln(\text{EC50}) - \text{slope} * \ln(\text{observed value})))}$$

The predicted concentrations are calculated as ln (concentration).

The maximum number of iterations performed to achieve convergence is 100, and the convergence criterion relative to Y values is 0.00000001.

The results of the inhibition assay are set forth in the following table.

| COMPOUND OF EXAMPLE NO. | Solvent | INHIBITION OF RSV (Ribavirin Control) | | ASSAY CONDITIONS | CTI▼ |
|---|---|---|---|---|---|
| | | HEp-2 ~CC50 (μM) | ~EC50 (μM) | | |
| Ex. 6 | DMSO | 100.3 | 24.7 | 5 day assay, drug added on day 1 only | 4.1 |
| Ex. 6 | PBS | 76245.6* | 247.8* | 5 day assay, drug added on day 1 only | 275.5 |
| Ex. 6 | DMSO | 155.5 | 58.1 | 5 day assay, drug added on day 1 only | 2.7 |
| Ex. 6 | PBS | 9397.1* | 431.1 | 6 day assay, drug added on day 1 only | 21.8 |
| Ex. 6 | DMSO | 365.1* | 250.2* | 6 day assay, drug added on day 1 only | 1.5 |
| Ex. 6 | PBS | # | 625.5* | 5 day assay, drug added on day 1 only | # |
| Ex. 6 | PBS | # | 45.0 | 5 day assay, drug replenished daily | # |
| Ex. 6 | PBS | # | 683.0* | 5 day assay, drug added on day 1 only | # |
| Ex. 6 | PBS | # | 184.6 | 5 day assay, drug replenished on day 3 | # |
| Ex. 6 | PBS | # | 228.3* | 5 day assay, drug added on day 1 only | # |
| ribavirin | water | 20.4 | 2.6 | 5 day assay, drug replenished on day 3 | 7.9 |
| ribavirin | water | 38.3 | 6.3 | 5 day assay, drug added on day 1 only | 6.1 |
| ribavirin | water | 32.432 | 6.470 | 5 day assay, drug added on day 1 only | 5.0 |
| ribavirin | water | 62.809 | 2.495 | 5 day assay, drug added on day 1 only | 25.2 |
| ribavirin | water | 179.304 | 19.089 | 6 day assay, drug added on day 1 only | 9.39 |
| ribavirin | water | 52.394 | 2.844 | 5 day assay, drug added on day 1 only | 18.4 |
| ribavirin | water | 40.0 | 0.1 | 5 day assay, drug replenished daily | 644.9 |

*extrapolated
no apparent toxicity, unable to extrapolate
▼CTI (cytotherapeutic index) = $\frac{\text{EC50}}{\text{CC50}}$ Example 45

An anti-RSV detection assay was carried out essentially as described in Example 44 except that each of the tested compounds was replenished daily at a single concentration of 200 μM for 5 days. Because serial dilutions were not used, the antiviral effect (% cell protection) and the cytotoxic effect (% cytotox.) were used directly to obtain the CTI. The results are reported in the following table.

| COMPOUND OF EXAMPLE NO. | SOLVENT | INHIBITION OF RSV (Ribavirin Control) | | % CELL PROTECTION | |
|---|---|---|---|---|---|
| | | % CELL PROTECTION | % CYTOTOXICITY | | % CYTOTOXICITY |
| EX. 43 | PBS | 102 | 10 | | 10 |
| EX. 6 | PBS | 54 | 17 | | 3.1 |
| EX. 7 | PBS | 6 | 11 | | 0.5 |
| Ribavirin | water | 106 | 65 | | 1.6 |

The compound of Ex. 7 is a prod rug which is enzymatically converted in vivo to the compound of Ex. 6.

Various other examples will be apparent to the person skilled in the art after reading the present disclosure without departing from the spirit and scope of the invention. It is intended that all such other examples be included within the scope of the appended claims.

What is claimed is:

1. A method for treating a mammal infected with respiratory syncytial virus (RSV) comprising administering to the mammal an RSV inhibitory effective amount of a compound or its pharmaceutically acceptable salt of the formula

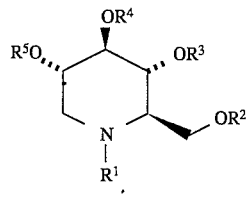

wherein $R^1$ is selected from the group consisting of H, linear or branched $C_1$–$C_{14}$ alkyl; $C_7$–$C_{14}$ aroyl; $C_7$–$C_{14}$ aralkyl, wherein the aryl moiety of the aralkyl or aroyl is optionally substituted with from 1 to 3 substituents selected from the group of $C_1$–$C_6$ alkyl, $C_1$–$C_6$ alkoxy, hydroxy, Cl, Br and F; and wherein $R^2$, $R^3$, $R^4$ and $R^5$ are independently selected from the group consisting of H and acyl group of the formula

wherein $R^6$ is a linear or branched $C_1$–$C_{10}$ alkyl, a $C_3$–$C_7$ cycloalkyl, or a $C_4$–$C_{10}$ (cycloalkyl)alkyl moiety.

2. A method according to claim 1 wherein $R^1$ is selected from the group of $C_1$–$C_9$ alkyl and $C_7$–$C_{14}$ aralkyl; and $R_2$, $R_3$, $R_4$ and $R_5$ are each H or $C_1$–$C_{10}$ acyl.

3. A method according to claim 2 wherein $R^1$ is $C_4$–$C_9$ alkyl.

4. A method according to claim 2 wherein $R^1$ is $C_7$–$C_{14}$ aralkyl.

5. A method according to claim 3 wherein $R^1$ is n-butyl.

6. A method according to claim 4 wherein $R^1$ is 3-phenylpropyl.

7. A method according to claim 1 wherein the RSV inhibitory effective amount of compound is administered orally.

8. A method according to claim 2 wherein $R^1$ is $C_1$–$C_9$ alkyl.

9. A method according to claim 2 wherein each of $R^2$, $R^3$, $R^4$ and $R^5$ is an acyl group.

10. A method according to claim 9 wherein $R^1$ is $C_4$–$C_9$ alkyl or $C_7$–$C_{14}$ aralkyl.

11. A method according to claim 2 wherein each of $R^2$, $R^3$, $R^4$ and $R^5$ is hydrogen.

12. A method according to claim 11 wherein $R^1$ is $C_4$–$C_9$ alkyl or $C_7$–$C_{14}$ aralkyl.

* * * * *

UNITED STATES PATENT AND TRADEMARK OFFICE
CERTIFICATE OF CORRECTION

PATENT NO. : 5,622,972

DATED : April 22, 1997

INVENTOR(S) : MARTIN L. BRYANT ET. AL.                    Page 1 of 2

It is certified that error appears in the above-identified patent and that said Letters Patent is hereby corrected as shown below:

COLUMN 9

Line 26, "silical" should read -- silica--
Line 60, "solvant" should read --solvent--

COLUMN 11

Line 45, "$C_{18}H_{29}NO_8$:" should read --$C_{18}H_{29}NO_8$:--

COLUMN 12

Line 7, "$C_{19}H_{27}NO_{11}$:" should read --$C_{19}H_{27}NO_{11}$:--

COLUMN 16

Line 18, "prepared" should read --prepared.--

COLUMN 19

Line 63, "(DSC 101° C.) Should read --(DSC 101°C.).--

COLUMN 23

Line 56, "$C_1, 7\cdot 33$;" should read --Cl, 7·33;--
Line 57, "$C_1, 7\cdot 35$;" should read --Cl, 7·35;--

UNITED STATES PATENT AND TRADEMARK OFFICE
CERTIFICATE OF CORRECTION

PATENT NO.  : 5,622,972

DATED       : April 22, 1997

INVENTOR(S) : MARTIN L. BRYANT ET. AL.

It is certified that error appears in the above-identified patent and that said Letters Patent is hereby corrected as shown below:

COLUMN 26

Line 41, "$EC_{50}$ and $CC_{50}$" should read --EC50 and CC50--
Line 58, "$EC_{50}$" should read --EC50--

COLUMN 27

Line 8, "$C=ln(EC_{50})$" should read --C = ln EC50--

COLUMN 29

Line 1, "prod rug" should read --prodrug--

Signed and Sealed this

Third Day of October, 2000

Attest:

Q. TODD DICKINSON

*Attesting Officer*          *Director of Patents and Trademarks*